US009354218B2

(12) United States Patent
Clark et al.

(10) Patent No.: US 9,354,218 B2
(45) Date of Patent: May 31, 2016

(54) APPARATUS AND METHOD FOR THE CHARACTERIZATION OF RESPIRABLE AEROSOLS

(71) Applicant: Consolidated Nuclear Security, LLC, Oak Ridge, TN (US)

(72) Inventors: Douglas K. Clark, Oak Ridge, TN (US); Bradley W. Hodges, Knoxville, TN (US); Jesse D. Bush, Knoxville, TN (US); Jofu Mishima, Oak Ridge, TN (US)

(73) Assignee: Consolidated Nuclear Security, LLC, Oak Ridge, TN (US)

(*) Notice: Subject to any disclaimer, the term of this patent is extended or adjusted under 35 U.S.C. 154(b) by 124 days.

(21) Appl. No.: 14/446,492

(22) Filed: Jul. 30, 2014

(65) Prior Publication Data

US 2016/0033466 A1    Feb. 4, 2016

(51) Int. Cl.
*G01N 33/20*    (2006.01)

(52) U.S. Cl.
CPC .................................. *G01N 33/20* (2013.01)

(58) Field of Classification Search
None
See application file for complete search history.

(56) References Cited

U.S. PATENT DOCUMENTS 6,327,889 B1 * 12/2001 Seltzer ................ G01N 1/2258
356/243.2

OTHER PUBLICATIONS

Aerosol Chemical Speciation Monitor, Aerodyne Research, http://www.aerodyne.com/products/aerosol-chemical-speciation-monitor.
Kanapilly et al., "A Method for Determining the Dissolution Characteristics of Accidentally Released Radioactive Aerosols," Proceedings of the Third International Congress of IRPA, pp. 1237-1242, Washington, DC, USAEC Document, C0NF-73907, 1973.
Fittschen et al, "Characterization of Atmospheric Aerosols using Synchrotron Radiation Total Reflection X-Ray Fluorescence and Fe K-edge Total reflection X-Ray Fluorescence X-Ray Absorption Near-Edge Structure," 63 Spectrochimica Acta Part B: Atomic Spectroscopy 12, pp. 1489-1495, Trento, Italy, Jun. 2007.

* cited by examiner

*Primary Examiner* — Robert Xu
(74) *Attorney, Agent, or Firm* — Clements Bernard PLLC; Christopher L. Bernard; Lawrence A. Baratta, Jr.

(57) ABSTRACT

An apparatus for the characterization of respirable aerosols, including: a burn chamber configured to selectively contain a sample that is selectively heated to generate an aerosol; a heating assembly disposed within the burn chamber adjacent to the sample; and a sampling segment coupled to the burn chamber and configured to collect the aerosol such that it may be analyzed. The apparatus also includes an optional sight window disposed in a wall of the burn chamber such that the sample may be viewed during heating. Optionally, the sample includes one of a Lanthanide, an Actinide, and a Transition metal.

12 Claims, 7 Drawing Sheets

FIG. 1

Table 1

| | Initial Mass | Δ Mass | Sampler Total | Coupon Wipe | Conc. U in Ash |
|---|---|---|---|---|---|
| U Run 1 | 1,169,143 mg | −643 mg | 2,247 µg | 3,930 µg | 19,100 µg/g |
| U Run 2 | 1,220,300 mg | −1,000 mg | 1,127 µg | 257 µg | 4,300 µg/g |
| U Run 3 | 1,269,690 mg | −390 mg | 507 µg | 254 µg | 1,510 µg/g |
| U Run 4 | 1,219,300 mg | +0 mg | 557 µg | 2,040 µg | 25,300 µg/g |
| U Run 5 | 1,168,500 mg | −1,079 mg | 4,153 µg | 1,890 µg | 52,300 µg/g |
| U-Ti Run 1 | 364,655 mg | −1,558 mg | 9,928 µg | 18,000 µg | 162,000 µg/g |
| U-Ti Run 2 | 380,071 mg | −209 mg | 5,956 µg | 13,200 µg | 11,500 µg/g |
| U-Ti Run 3 | 435,347 mg | −357 mg | 10,953 µg | 2,070 µg | 50,000 µg/g |
| U-Ti Run 4 | 310,582 mg | −506 mg | 41,147 µg | 46,500 µg | 49,600 µg/g |
| U-Ti Run 5 | 360,645 mg | −407 mg | 2,254 µg | 2,680 µg | 30,800 µg/g |
| U-Nb Run 1 | 1,046,643 mg | +230 mg | 40 µg | Non-detect | 1,860 µg/g |
| U-Nb Run 2 | 1,090,040 mg | −7 mg | 21 µg | Non-detect | 179 µg/g |
| U-Nb Run 3 | 1,143,040 mg | −430 mg | 52 µg | Non-detect | 114 µg/g |
| U-Nb Run 4 | 1,090,033 mg | +6 mg | 173 µg | 6.59 µg | 2,030 µg/g |
| U-Nb Run 5 | 1,090,039 mg | +26 mg | 67 µg | 6.57 µg | 344 µg/g |

*FIG. 2*

Table 2

|  | Stage 0 | 1 | 2 | 3 | 4 | 5 | 6 | 7 | Final Filter |
|---|---|---|---|---|---|---|---|---|---|
| U Run 1 | 436 μg | 170 μg | 54 μg | 16 μg | 10 μg | 4 μg | 2 μg | 1 μg | 3 μg |
| U Run 2 | 262 μg | 43 μg | 15 μg | 10 μg | 6 μg | 2 μg | 5 μg | 2 μg | 3 μg |
| U Run 3 | 76 μg | 16 μg | 9 μg | 5 μg | 6 μg | 3 μg | 4 μg | 3 μg | 5 μg |
| U Run 4 | 272 μg | 79 μg | 17 μg | 12 μg | 7 μg | 5 μg | 4 μg | 6 μg | 5 μg |
| U Run 5 | 796 μg | 223 μg | 28 μg | 29 μg | 20 μg | 13 μg | 9 μg | 5 μg | 40 μg |
| U-Ti Run 1 | 1,940 μg | 1,050 μg | 283 μg | 179 μg | 60 μg | 29 μg | 15 μg | 15 μg | 18 μg |
| U-Ti Run 2 | 547 μg | 535 μg | 91 μg | 44 μg | 26 μg | 19 μg | 14 μg | 28 μg | 22 μg |
| U-Ti Run 3 | 2,870 μg | 840 μg | 104 μg | 65 μg | 45 μg | 37 μg | 20 μg | 30 μg | 32 μg |
| U-Ti Run 4 | 223 μg | 115 μg | 35 μg | 27 μg | 14 μg | 11 μg | 9 μg | 7 μg | 9 μg |
| U-Ti Run 5 | 188 μg | 138 μg | 49 μg | 33 μg | 23 μg | 14 μg | 10 μg | 12 μg | 6 μg |
| U-Nb Run 1 | 5 μg | 3 μg | 2 μg | 3 μg | 2 μg | 2 μg | 3 μg | 12 μg | 3 μg |
| U-Nb Run 2 | 3 μg | 1 μg | 1 μg | 2 μg | 1 μg | 1 μg | 1 μg | 1 μg | 1 μg |
| U-Nb Run 3 | 6 μg | 4 μg | 2 μg | 1 μg | 24 μg | 1 μg | 2 μg | 2 μg | 4 μg |
| U-Nb Run 4 | 70 μg | 47 μg | 17 μg | 9 μg | 4 μg | 3 μg | 5 μg | 1 μg | 3 μg |
| U-Nb Run 5 | 9 μg | 7 μg | 6 μg | 4 μg | 3 μg | 2 μg | 4 μg | 3 μg | 6 μg |

*FIG. 3*

Table 3

| Stage | 0 | 1 | 2 | 3 | 4 | 5 | 6 | 7 |
|---|---|---|---|---|---|---|---|---|
| Cutoff Diameter | 10 μm | 9 μm | 5.8 μm | 4.7 μm | 3.3 μm | 1.1 μm | 0.65 μm | 0.43 μm |
| Temp. Correction | 0.9 μm | 0.8 μm | 0.5 μm | 0.4 μm | 0.3 μm | 0.1 μm | 0.06 μm | 0.04 μm |

Table 4

| Parameter | Geometric Mean | | | Arithmetic Average | | |
|---|---|---|---|---|---|---|
| | U-Ti | U | U-Nb | U-Ti | U | U-Nb |
| Impactor Total Mass | 1,324 µg | 429 µg | 44 µg | 1,975 µg | 548 µg | 61 µg |
| Total Mass in Sampler | 9,030 µg | 1,243 µg | 55 µg | 14,047 µg | 1,718 µg | 70 µg |
| Coupon Wipe Mass | 16,254 µg | 998 µg | 7 µg | 25,874 µg | 1,674 µg | 7 µg |
| Conc. U in Ash | 41,156 µg/g | 11,041 µg/g | 484 µg/g | 63,575 µg/g | 20,502 µg/g | 905 µg/g |
| \|Δ Mass\| | 474 mg | 674 mg | 40 mg | 607 mg | 519 mg | 35 mg |

FIG. 6

Table 5

| Parameter | Geometric Mean | | | Arithmetic Average | | |
|---|---|---|---|---|---|---|
| | U-Ti | U | U-Nb | U-Ti | U | U-Nb |
| $ARF_{metal}$ | $2 \times 10^{-5}$ | $1 \times 10^{-6}$ | $5 \times 10^{-8}$ | $4 \times 10^{-5}$ | $1 \times 10^{-6}$ | $6 \times 10^{-8}$ |
| RF | 47% | 33% | 77% | 49% | 33% | 78% |
| $ARF \times RF_{metal}$[a] | $1 \times 10^{-5}$ | $3 \times 10^{-7}$ | $4 \times 10^{-8}$ | $2 \times 10^{-5}$ | $5 \times 10^{-7}$ | $5 \times 10^{-8}$ |
| Fume : Ash Ratio[b] | $3.1 \times 10^{-3}$ | $1.6 \times 10^{-3}$ | $1.6 \times 10^{-3}$ | $3.2 \times 10^{-3}$ | $1.2 \times 10^{-3}$ | $1.1 \times 10^{-3}$ |

[a] ARF×RF is not the product of the mean ARF and mean RF, but the mean of the ARF × RF products.
[b] Fume : Ash Ratio = total mass in sampler ÷ [concentration U in ash × 71 g (mean mass of ash)].

APPARATUS AND METHOD FOR THE CHARACTERIZATION OF RESPIRABLE AEROSOLS

STATEMENT REGARDING FEDERALLY SPONSORED RESEARCH OR DEVELOPMENT

The U.S. Government has rights to the present disclosure pursuant to Contract No. DE-NA0001942 between the U.S. Department of Energy and Consolidated Nuclear Security, LLC.

FIELD OF THE DISCLOSURE

The present disclosure relates generally to the characterization of respirable aerosols, and especially the characterization of toxic Lanthanides, Actinides, and Transition metals. More specifically, the present disclosure relates to an apparatus and method for the characterization of respirable aerosols that is inexpensive to construct and that enables enhanced data fidelity.

BACKGROUND OF THE DISCLOSURE

Although regulations have changed significantly since the 1980s, and technology has advanced in general, the apparati and methods used in the characterization of toxic respirable aerosols have not. Thus, what are still needed in the art are apparati and methods that incorporate the strengths of conventional small-scale indoor experiments with the desired characteristics of conventional large-scale outdoor experiments. By incorporating the lessons learned from previous experiments with desired characteristics that have resulted in low-fidelity data with modern quality requirements, computational fluid dynamics evaluation, and modern consensus codes and standards for sampling, a single low-cost apparatus and method may be developed that offers the needed characterization capabilities at a fraction of the cost of previous experiments, while accommodating chemical forms that were previously untestable.

BRIEF SUMMARY OF THE DISCLOSURE

Thus, in various exemplary embodiments, the present disclosure provides an apparatus and method that incorporates the strengths of conventional small-scale indoor experiments with the desired characteristics of conventional large-scale outdoor experiments, and that offers the needed characterization capabilities at a fraction of the cost of previous experiments, while accommodating chemical forms that were previously untestable. The use of internal heating, instead of heating external to the apparatus, is a significant contribution of the present disclosure. The present disclosure also allows for greater control in the amount of heating and the method of heating, i.e., conductive, radiant, and/or convective, while conventional apparati were limited to radiant (indoors) and convective (outdoors). Additionally, the present disclosure makes use of a valuable sight window.

The apparatus and method of the present disclosure were developed primarily for the characterization of the metal forms of the toxic Lanthanides, Actinides, and Transition metals. This technology, however, is readily adaptable for use with other solid, liquid, and aerosol forms, including those that have previously been unsuitable for testing, as is apparent to those of ordinary skill in the art. The fact that the cost of the apparatus has been reduced orders of magnitude from previous apparati and the cost for testing has been similarly reduced to levels typically associated with a standard ASTM test, provides the ability for universities and third party test centers to expand the current limitations on testing and test materials to be comparable to those of large governmental or international agencies.

Any group that tries to characterize the formation of respirable aerosols would benefit from the use of the apparatus and method of the present disclosure. For example, this technology could be adapted by pharmaceutical companies or drug enforcement companies that want to understand fires involving pharmaceuticals and/or contraband. Such groups benefit from being able to determine the characteristics of their product material and modify it to either enhance or reduce its tendency to form a respirable aerosol.

In one exemplary embodiment, the present invention provides an apparatus for the characterization of respirable aerosols, including: a burn chamber configured to selectively contain a sample that is selectively heated to generate an aerosol; a heating assembly disposed within the burn chamber adjacent to the sample; and a sampling segment coupled to the burn chamber and configured to collect the aerosol such that it may be analyzed. The apparatus also includes an optional sight window disposed in a wall of the burn chamber such that the sample may be viewed during heating. The burn chamber includes a first burn chamber coupled to a second burn chamber. The second burn chamber includes a gas intake conduit operable for introducing a gas into the burn chamber. The burn chamber also includes a first spacer disposed therein, the first spacer operable for determining a position of the heating assembly and the sample within the burn chamber. The burn chamber further includes a second spacer disposed therein adjacent to the first spacer, the second spacer selectively containing a combustible material that is selectively burned and operable for determining the position of the sample within the burn chamber. The burn chamber still further includes a grate disposed between the first spacer and the second spacer. The sample is selectively disposed on and supported by the second spacer. The heating assembly is disposed between the first spacer and the second spacer. Optionally, the heating assembly includes a spiral heater disposed between a ceramic disc and a quartz disc, the quartz disc operable for preventing the spiral heater from directly contacting the combustible material disposed adjacent to the heating assembly that is selectively burned. The sampling segment includes an aerosol offtake conduit operable for communicating a portion of the aerosol selectively present in the sampling segment to an attached aerosol analyzing system. The sampling segment also includes a filter disposed at an end thereof opposite the burn chamber. Optionally, the sample includes one of a Lanthanide, an Actinide, and a Transition metal.

In another exemplary embodiment, the present invention provides a method for the characterization of respirable aerosols, including: providing a burn chamber configured to selectively contain a sample and selectively heating the sample to generate an aerosol; providing a heating assembly disposed within the burn chamber adjacent to the sample; and providing a sampling segment coupled to the burn chamber and collecting the aerosol such that it may be analyzed. The method also including viewing the sample during heating through an optional sight window disposed in a wall of the burn chamber. The burn chamber includes a first burn chamber coupled to a second burn chamber. The second burn chamber includes a gas intake conduit operable for introducing a gas into the burn chamber. The burn chamber also includes a first spacer disposed therein, the first spacer operable for determining a position of the heating assembly and the sample within the burn chamber. The burn chamber further includes a second spacer disposed therein adjacent to the first spacer, the second spacer selectively containing a combustible material that is selectively burned and operable for determining the position of the sample within the burn chamber. The burn chamber still further includes a grate disposed between the first spacer and the second spacer. The sample is selectively disposed on and supported by the second spacer. The heating assembly is disposed between the first spacer and the second spacer. Optionally, the heating assembly includes a spiral heater disposed between a ceramic disc and a quartz disc, the quartz disc operable for preventing the spiral heater from directly contacting a combustible material disposed adjacent to the heating assembly that is selectively burned. The sampling segment includes an aerosol offtake conduit operable for communicating a portion of the aerosol selectively present in the sampling segment to an attached aerosol analyzing system. The sampling segment also includes a filter disposed at an end opposite the burn chamber. Optionally, the sample includes one of a Lanthanide, an Actinide, and a Transition metal.

BRIEF DESCRIPTION OF THE DRAWINGS

The present disclosure is illustrated and described herein with reference to the various drawings, in which like reference numbers are used to denote like apparatus components/method steps, as appropriate, and in which.

DETAILED DESCRIPTION OF THE DISCLOSURE

In the present disclosure, aerosols dispersed from the oxidation of various uranium alloys exposed to air and direct flame impingement from combustible substrates are characterized. An apparatus is provided that incorporates the desired characteristics of previous experiments with uranium to sample aerosols on a kilogram scale in a laboratory environment. Previous studies involving β-phase stabilized uranium (99.25 wt % U: 0.75 wt % Ti) were benchmarked using identical alloys with identical characteristics to the original specimens. Other studies involving α-phase uranium (100 wt % U) were also benchmarked in this experiment. Unique to this study is the use of γ-phase stabilized uranium (94 wt % U: 6 wt % Nb). These three alloys represent the crystallographic range of typical uranium metals, providing a complete spectrum of potential uranium aerosolization. Oxidation rates and extents observed in these experiments are directly comparable to existing data and provide correlation between previous studies. These experiments indicate a distinct order-of-magnitude difference between uranium alloy (β, α, γ) responses to thermal stress.

The primary purpose of these experiments is to characterize the nature and amount of uranium aerosol dispersed if uranium metal is involved in a fire, for example. The use of uranium as a nuclear fuel continues to increase globally, concurrent with global initiatives to convert research reactors and isotope production facilities from the use of highly-enriched uranium to low-enriched uranium. The net effect is an increase in the amount of uranium-bearing fuels being manufactured, stored, and transported on a global scale. Understanding the thermal response of uranium metal and alloys is essential to protecting public health, safety, and the environment. Unfortunately, only a minimal amount of experimental data exists on the formation and release of respirable oxide fumes from uranium alloys.

Two main guidance documents that exist for quantifying the release of respirable oxide are the American National Standard for Airborne Release Fractions at Non-Reactor Nuclear Facilities (ANSI 1998) and the Department of Energy's Handbook of Airborne Release Fractions/Rates and Respirable Fractions for Nonreactor Nuclear Facilities (DOE 1994). Both documents were principally authored by the late Dr. Jofu Mishima using the same sets of reference experiments. The bounding airborne respirable release fraction of $1 \times 10^{-3}$ for uranium aerosol comes from experiments conducted by Elder and Tinkle on β-phase stabilized depleted uranium specimens containing 0.75 wt % titanium at Los Alamos National Laboratories, Los Alamos, N. Mex. (Elder 1980). Also reported is a median airborne respirable release fraction of $1 \times 10^{-4}$ for uranium aerosol from experiments conducted by Carter and Stewart on α-phase uranium at the Atomic Weapons Research Establishment, Berkshire, England (Carter 1970). These values are an order of magnitude apart, indicating a potential difference in alloy specific responses to thermal stress.

The approach taken in the present disclosure is to measure the fractional airborne release and aerodynamic size distribution differences between categories of uranium metal and alloys. Pure uranium has three normal metallurgical phases, ranging from ductile semi-plastic response to brittle fracture under thermal stress scenarios. Uranium alloys allow specific metallurgical phases to be frozen, preserving desired metallurgical characteristics. By subjecting uranium metal and alloys to identical thermal stress, the relative difference in response of each alloy can be quantified. The resultant differences in fractional airborne release between alloys are important in proper characterization of the hazards associated with manufacturing, transportation, and storage of uranium bearing materials. The present disclosure looks for distinct order-of-magnitude differences between the dominant alloys representing distinct metallurgical phases.

Uranium is a pyrophoric material, but sustains burning only in finely divided form (e.g., dispersed small fragments or fine turnings). A respirable oxide fume of uranium can have significant toxicological effects leading to renal failure. The radiological effects of uranium are dependent on the enrichment level. For depleted uranium, used in the present disclosure, there is negligible radiological effect. The influence of nephrotoxicity on urinary excretion of uranium indicates that kidney concentrations of 3 µg uranium per g of kidney correlates to kidney damage in humans (Hodgson 2007). The International Commission on Radiological Protection's Publication 2 (1959) uses a nominal kidney mass of 300 g and a fraction of uranium in the kidneys relative to that in the total body of 0.065. As such, an uptake of 30 mg soluble uranium may lead to renal failure. One of the runs in this experiment (U—Ti run 4) exceeded 30 mg U aerosol in the sampling segment, representing a toxicological hazard.

To represent the α-phase (i.e., metallurgical phase) in these experiments, pure depleted uranium consisting of α-annealed uranium with only trace quantities of other elements (i.e., less than 20 ppm) was formed into billets and sheared into nominally 1-inch by 2-inch by 2-inch specimens. This is the same form of uranium used by Carter and Stewart in their experiments (Carter 1970). To represent the β-phase in these experiments, an alloy of 99.25 wt % uranium with 0.75 wt % titanium was immersion quenched in water from the γ-phase that was subsequently aged in a furnace to produce a pure β-phase stabilized alloy. The water quenching process produces nominally 2 ppm hydrogen during aging, with less than 20 ppm other contaminants. In this study, the use of U—Ti refers specifically to this preparation. This is the same preparation used by National Lead of Ohio to prepare the U—Ti specimens used in the Elder and Tinkle Experiment (Zabielski 1994). To represent the γ-phase in these experiments, an alloy of 94 wt % uranium with 6 wt % niobium was produced by vacuum induction melting depleted uranium around a niobium core, then vacuum arc re-melting this electrode configuration into billets, which were then used as electrodes in a second vacuum arc re-melting. This produces a homogenous U—Nb mixture that is γ-phase stabilized with less than 20 ppm contaminants. In this study, the use of U—Nb refers specifically to this preparation.

Figure 1:
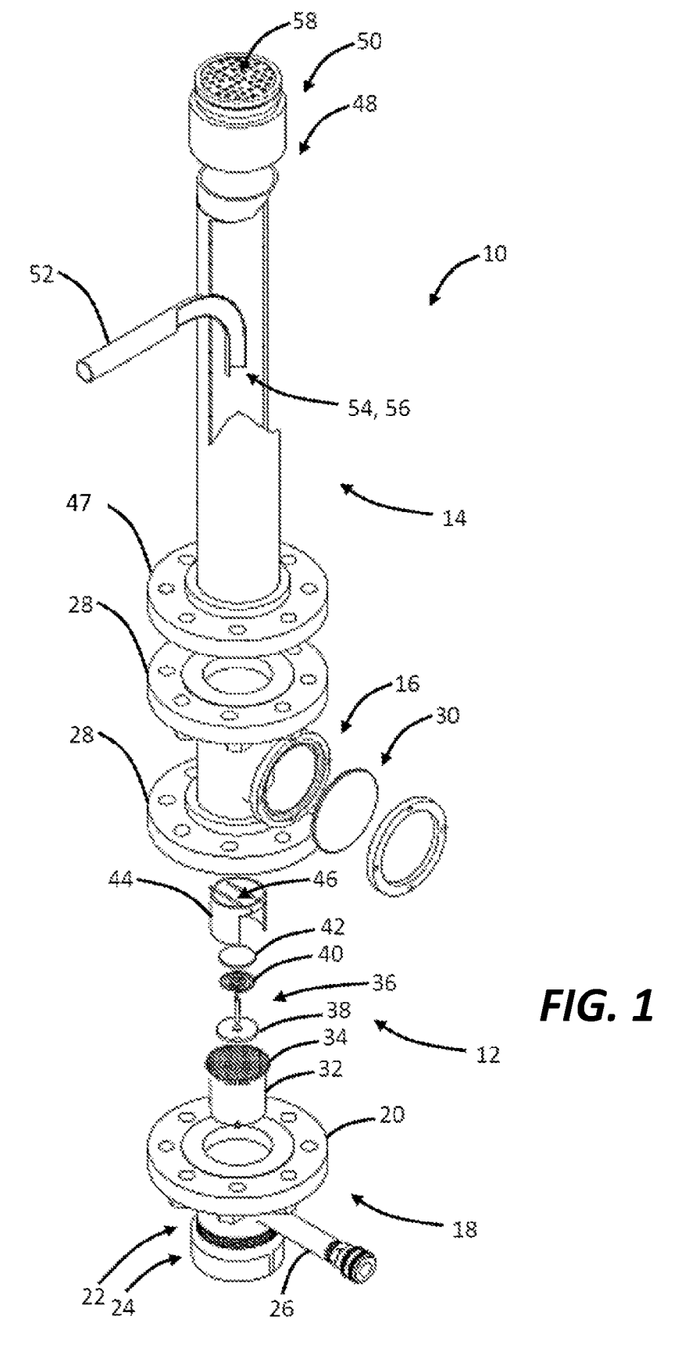
FIG. 1 is an exploded schematic diagram illustrating one exemplary embodiment of the apparatus for the characterization of respirable aerosols of the present disclosure.

Referring now specifically to FIG. 1, in one exemplary embodiment, the apparatus 10 of the present disclosure utilizes a custom designed burn chamber 12 and sampling segment 14 that incorporate the requirements of ASME NQA-1 2008 and ANSI/HPS-N13.1-1999. The burn chamber 12 consists of two pieces 16 and 18 of nominally a 10-cm (4-inch) diameter, 25-cm (10-inch) long schedule 40 pipe. The lower section 18 contains a 4-inch flange connection 20 on the downstream side and an NPT connection 22 on the upstream side with a 4-inch end-cap 24 installed. The lower section 18 has a 1-inch-diameter pipe 26 inserted through the bottom end and curving into the centerline of the pipe segment with a curvature ratio (i.e. radius of curvature of the bend divided by the tube diameter) of 1.0. The upper section 16 contains a 4-inch flange connection 28 on each side and a 3-inch-diameter quartz sight window 30 welded into the middle of this section in a "T" shape for observation of the uranium piece. Each section is bolted to adjacent sections using a compressible gasket (rated for 1000° C.) and standard 304L stainless steel bolts, for example.

The uranium specimen is suspended over the combustible material using a pair of semi-adjustable spacers 32 and 44 that are used to situate flame impingement against the specimen and orient the specimen for viewing through the sight window 30. The lower spacer 32 is covered by expanded metal mesh 34 and is used to support the heating element 36 and charcoal. Atop the mesh 34 sits a ceramic disk 38 with a spiral resistance heater 40 capable of maintaining temperatures of 1380° C. [MC-GAXP-130, MHI6AXP Spiral Microheater (Micropyretics Heaters International, Cincinnati, Ohio)]. This heater 40 is used to ignite the charcoal. Between the charcoal and the heater is a small quartz disk 42 that distributes the heat and allows expansion/contraction of the heating element 40. The charcoal is located beneath the uranium specimen and above the quartz disk 42. The upper spacer 44 is a nominally 3-inch, 16-gauge stainless steel pipe segment with two 18-gauge tungsten wires 46 spanning the circumference that supports the specimen while not hindering flame impingement on the specimen.

The sampling segment 14 is constructed from a 10-cm (4-inch)-diameter, 46-cm (18-inch)-long schedule 40 pipe or the like with a 4-inch flange connection 47 on the upstream side and an NPT connection 48 on the downstream side with a 4-inch gross filter holder 50 installed. The sampling segment 14 also has a 1-inch-diameter pipe 52 inserted through the bottom end and curving into the centerline of the pipe segment 14 with a curvature ratio (i.e., radius of curvature of the bend divided by the tube diameter) of 3.0. The inlet 54 of the sampling nozzle 56 is 6 inches back from the inlet of the sampling segment 14, oriented parallel to the centerline of the pipe 14. The leading edge of the nozzle 56 has a sharp edge with the external cone angle of 30°. The nozzle 56 is constructed from stainless steel and does not have a rake. To the 1-inch pipe 52, an eight-stage ambient sampler with 10-μm pre-cutters is attached [Model 20-800 Ambient Cascade Impactor (Non-Viable) (Tisch Environmental, Inc., Cleves, Ohio)]. Normal impactor sampling flow rate is 28.3 L/min (1 cfm) at ambient conditions (approximately 775 mb and 20° C.) with sensitivity of ±1.5 L/min at 200° C. The sampling segment 14, minus the cascade impactor, is fabricated by the Hi-Q Environmental Products Company in San Diego, Calif., for example.

In operation, the procedure for conducting each run was identical, so that the principal variable between runs was the composition of the uranium specimen. Each run was started with a cleaned apparatus 10 that held less than 0.5 μg residual uranium. A single 4-inch binderless, high-efficiency (HEPA type), high-purity, 100% high-quality borosilicate glass micro fiber filter media 58, rated for temperatures up to 600° C., with a DOP (dioctyl phthalate) Collection Efficiency of 99.99% for 0.3 μm aerodynamic equivalent diameter [FPAE-102 (Hi-Q Environmental Products Company, San Diego, Calif.)] is held in place across the 102-mm (4-inch) schedule 40 pipe 14 with a screw compression Teflon gasket. Next, 81-mm glass fiber filter media [TE-20-301 Glass Fiber Substrate Discs (Tisch Environmental, Cleves, Ohio)] are loaded into each stage of the cascade impactor. Three pieces of Kingsford Original Brand charcoal briquettes (Clorox Company, Oakland, Calif.), weighing 23.6±0.4 g per briquette, are loaded into the burn chamber 12. The uranium specimen is then loaded above the briquettes, and the apparatus 10 is sealed tight.

An airflow rate of 14.2±0.2 scfm is established into the burn chamber 12, and the vacuum pump pulling 28.3±1.5 L/min is turned on. Next, power is applied to the heating element 36, which in turn ignites the charcoal. The charcoal is allowed to burn to extinction. One hour after the heating element 36 is turned on, the vacuum pump is turned off. Once the apparatus 10 has cooled to <40° C., airflow to the apparatus 10 is turned off. The apparatus 10 is then disassembled and cleaned. The uranium specimen is hand cleaned of all readily removable oxide. Wipes and filter media from each section of the apparatus 10 are collected for analysis. Residual ash from the apparatus 10 is collected for observation and analysis.

Particle size characterization obtained during the experiments was obtained using the cascade impactor. The effect of gas temperature on impactor calibration was not corrected for, owing to expected difficulty in measuring gas temperature at each impaction stage in each experiment. The maximum error in the effective cutoff diameter (largest at the pre-cutter and stage 0) would be proportional to viscosity, where the viscosity of air increases from 185 micropoises (µP) at 25° C. (calibration temperature) to 220 µP at 100° C. (measured maximum at Stage 1 during the laboratory experiments). The maximum correction factor applied to the pre-cutter and the first few impactor stages in this case would be approximately 1.09 or <10% error in effective cutoff diameter, which is not significant in this instance. The effective cutoff diameter of the pre-cutter is increased from 9-10 µm to 10-11 µm, which skews the fraction of aerosol less than 10 µm in a conservative direction.

All borosilicate glass filter media and ash samples were dissolved in a nitric acid solution. The uranium was extracted from the nitric acid solution by vacuum aspiration over a chromatographic column containing 40% (w/w) diamyl amlyphosphonate on Amberlite XAD-7 or Amberchrom CG-71 ms. The column is washed with nitric acid solution to elute most other sample constituents. The uranium is eluted from the column with deionized water, and the eluate taken to dryness on a hotplate. The samples were loaded onto rhenium or tantalum filaments and analyzed using a Finnigan Triton 2 Thermal Ionization Mass Spectrometer. The minimum detectable uranium by this method is 0.15 µg.

Figure 2:
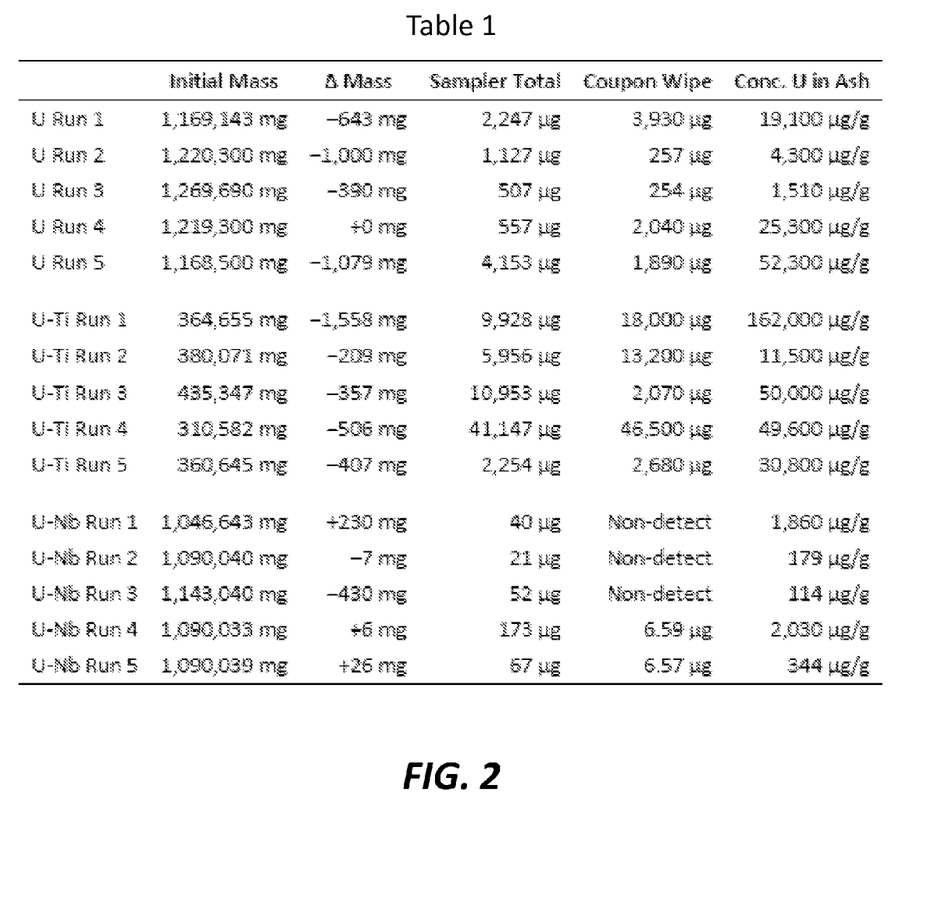
FIG. 2 is a table summarizing exemplary data related to coupon oxidation and oxide collection in association with the apparatus of FIG. 1.

The masses of uranium oxide collected in sample locations combined with the mass balance on the metal coupon quantify the thermal response for each of the 15 experimental runs summarized in Table 1 of FIG. 2. The initial mass of the coupons was measured in milligrams, whereas aerosolized oxide values are reported in micrograms. Positive values of the mass delta indicate adherent oxide not mechanically separable from the base coupon. All 15 experimental runs utilized the same specific area (i.e., surface area-to-mass ratio), although the initial mass of the U—Ti is one-third of other alloys. U—Ti alloy was the rarest and most difficult to obtain; therefore, the smaller mass was an attempt to conserve the amount of alloy available.

Observation of the oxidation runs in Table 1 was conducted through the quartz sight window. Generally, the pure uranium sparked occasionally for 5-7 minutes while the U—Ti alloy sparked almost continually for a similar duration. The U—Nb alloy was only observed to spark in U—Nb Run 3 where a burr on the edge of the coupon separated from the coupon in a single spark event.

For each of the 15 runs, the aerosol in the sampler was processed through the cascade impactor. The filter media from the impactor was analyzed for mass of uranium, as reported in Table 2 of FIG. 3. All values in Table 2 have been reported to the nearest µg, although measured to the nearest 0.01 µg.

Figure 3:
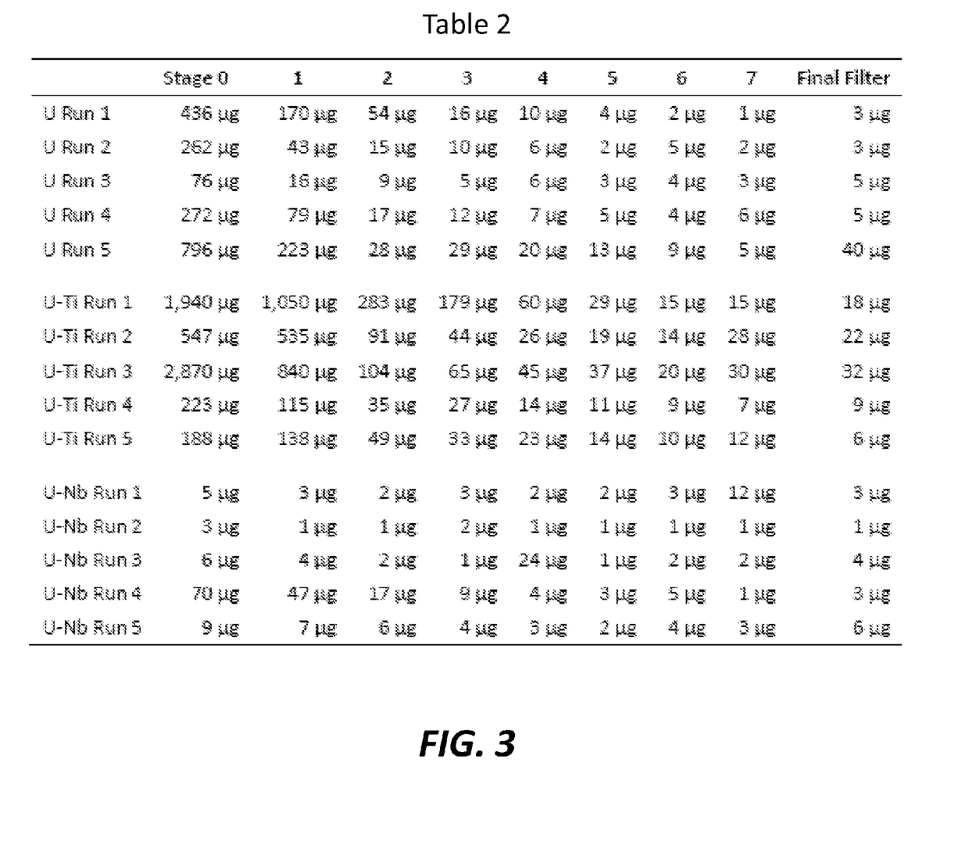
FIG. 3 is a table summarizing exemplary data related to the mass of uranium collected in each stage of a cascade impactor in association with the apparatus of FIG. 1.
Figure 4:
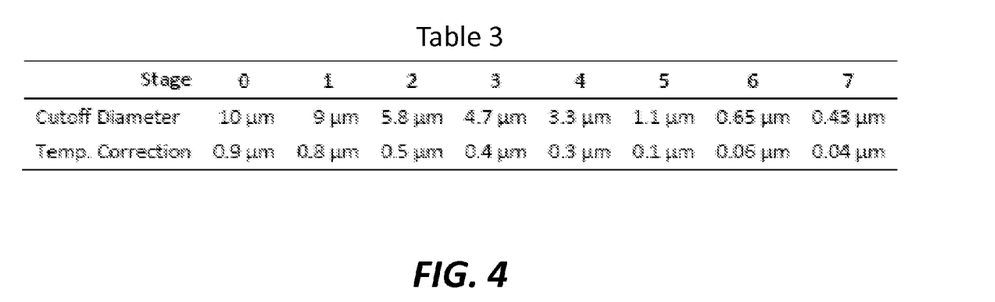
FIG. 4 is a table summarizing exemplary data related to the effective cutoff diameters in the cascade impactor in association with the apparatus of FIG. 1.
Figure 5:
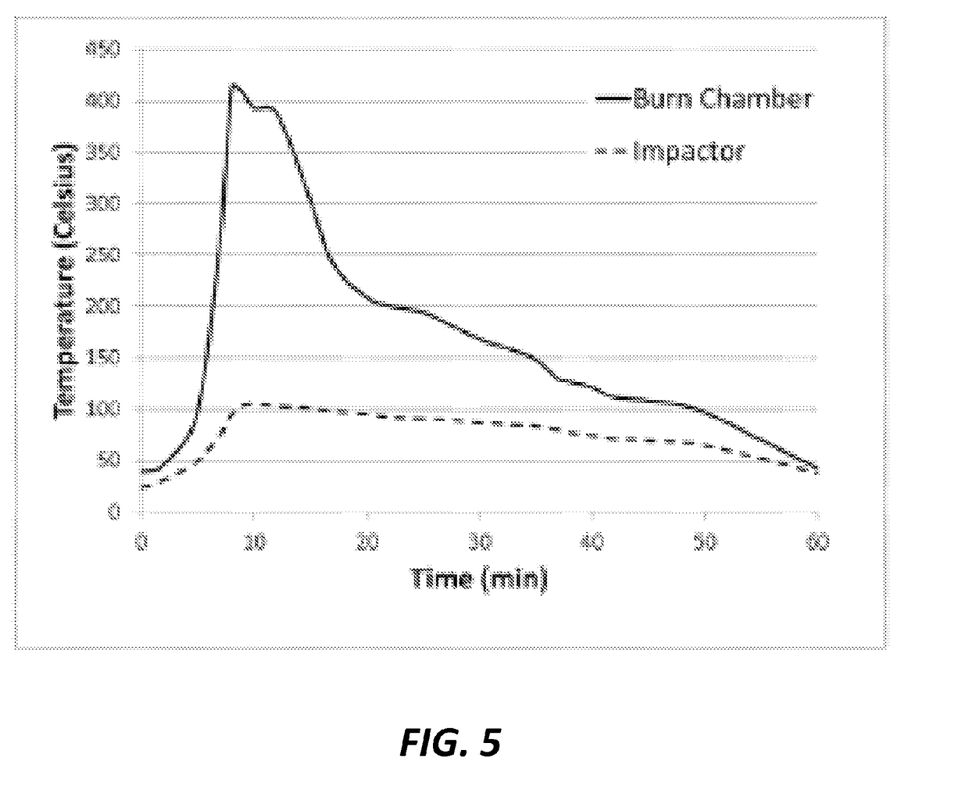
FIG. 5 is a graph summarizing exemplary data related to the peak measured air temperatures in association with the apparatus of FIG. 1.

The impactor stages reported in Table 2 correspond to effective cutoff diameters shown in Table 3 of FIG. 4. The temperature corrections based on the maximum temperatures observed in the sampling segment are included in Table 3. The air temperatures measured in the burn chamber and at the impactor sampling location are shown in FIG. 5. The temperature measured in the sampling segment was used to determine the impact on the effective cutoff diameter of the cascade impactor and to monitor exhaust temperatures.

Previous experiments assessing the amount of respirable aerosol likely to be released in a fire involving the oxidation of uranium metals have employed the use of geometric means and 95% confidence limits. The maximum values for the dataset in Tables 1 and 2 are compared to the 95% confidence limits and the geometric means of that dataset are reported in Table 4 of FIG. 6 for comparison with previous experiments.

Figure 6:
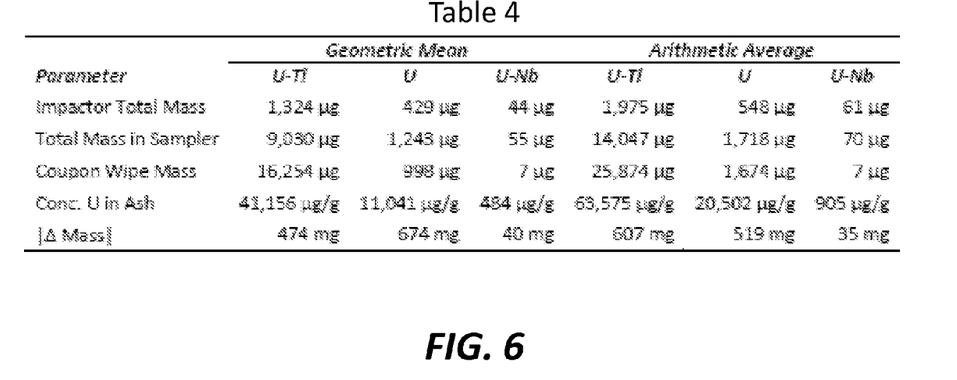
FIG. 6 is a table summarizing exemplary data related to various experiments by alloy in association with the apparatus of FIG. 1.

Table 4 demonstrates a distinctly different thermal response from each of the alloys. The U—Nb alloy experienced markedly less oxidation and aerosol. The mass delta associated with oxidation of U—Ti covered the same range as the oxidation of the pure U with markedly higher amounts of aerosol and mechanically separable oxide from the coupon. The experimental data indicates the amount of respirable oxide is highly alloy dependent with nominally order-of-magnitude differences. The representative airborne release fraction (ARF) for the metal is taken as the total mass in the sampler divided by the initial mass of the metal coupon. The respirable fraction (RF) of the aerosol consists of the total mass collected on stages 1-7 plus the final filter divided by the total impactor mass. Table 5 of FIG. 7 reflects the ARF, RF, and resultant product reflecting the airborne respirable release fraction (ARF×RF).

The Elder and Tinkle (1980) experiments have a geometric mean ARF of $1\times10^{-4}$, RF of 50%, and ARF×RF of $7\times10^{-5}$. These values represent the sampling during outdoor burn test #4 in those experiments. The maximum values from Elder and Tinkle outdoor burn test #4 were an ARF of $9\times10^{-4}$, RF of 62%, and ARF×RF of $6\times10^{-4}$. From Table 4, the geometric mean values are comparable between these experiments and the Elder and Tinkle outdoor burn test #4, while the RF values are identical. The maximum values with an ARF of $1\times10^{-4}$ and RF of 60% from Table 4 are also comparable to the Elder and Tinkle experiment. Subsequently, the close alignment between these values indicates appropriate benchmarking of these experiments against those previous studies.

The previous studies by Carter and Stewart (1970) have noted, "it is clear that the sparking phenomenon is the primary source of the fume fraction of the aerosol in all the dynamic experiments, and if the events where sparking was particularly evident are considered as a distinct group, the data fall within fairly well-defined limits." Carter and Stewart reported geometric mean and 95th percentile fractions of source material releases as aerosols from partial disruption of liquid into droplets. The geometric mean values are $3.5\times10^{-3}$ for Pu and $1.9\times10^{-3}$ for α-phase U, while the 95th percentile values are $1\times10^{-2}$ for Pu and $6\times10^{-3}$ for α-phase U.

Figure 7:
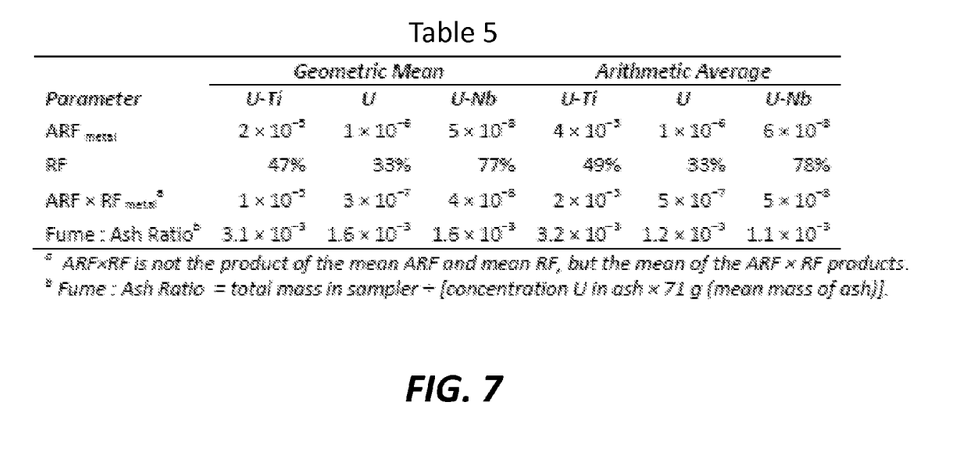
FIG. 7 is a table summarizing exemplary data related to representative release fractions and limits by alloy in association with the apparatus of FIG. 1.

Acknowledging that temperatures associated with visible sparking are associated with liquid metals, this work directly correlates the aerosol from each of the sparks to the aerosol from partial disruption of liquid droplets. Normalization of the data in Table 4 to an ash:fume ratio is made for direct comparison to the partial disruption of liquid droplets wherein the total mass in the sampler is divided by the product of the uranium concentration in the ash and the average ash mass (i.e., 71 g ash). As shown in Table 5, this normalization indicates that U—Ti (β-phase U) responds similarly to Pu, while α-phase U and U—Nb (γ-phase uranium) respond similarly to U in previous experiments. The maximum release for β-phase U was $1.2\times10^{-2}$ associated with U—Ti Run 4. The maximum release for α-phase U was $4.7\times10^{-2}$ associated with pure U Run 3, while for γ-phase U was $6.4\times10^{-3}$ associated with U—Nb Run 3. These values indicate there is a correlation between the U—Ti and Pu from the Carter and Stewart (1970) experiments, while U—Nb and pure U correlate to the α-phase U.

Looking for a correlation between U—Ti and Pu leads to consideration of the crystallographic structure for the alloys. The Pu in the Carter and Stewart (1970) experiments consists of 144 mg metal rods that had been heated to 660° C. and were dropped 0.75 m in an Ar atmosphere. As such, the correlation between a liquid Pu and solid U—Ti is not readily apparent. X-ray diffraction studies conducted at Oak Ridge National Laboratory (ORNL) show the crystallographic orientation of the different phase-stabilized alloys tested in this study (Yakel 1974). The number of atoms in each unit cell for each of the alloys range from two for the γ-phase U—Nb to 30 for the β-phase U—Ti, with pure U having four in the α-phase.

Plutonium, being a particularly interesting metal, has many metallurgical phases in the solid state and can have non-linear response to thermal stress. Lawson describes the number of atoms in a unit cell for plutonium can be 34 for the β-phase up to 58 for the ζ-phase, which contains at least 10 crystallographically distinct Pu atom types (Lawson 2006). Subsequently, if Pu liquid droplets were separated from ζ-phase Pu, the substrate would have 34 to 68 atoms per unit cell. Consequently, liquid droplets of Pu are comparable to U—Ti.

The Carter and Stewart experiments also reported airborne respirable release fractions for ignition and burning of metal in air with a geometric mean ARF×RF of $1.1\times10^{-4}$ and a 95% confidence limit ARF×RF of $3.6\times10^{-4}$. The specific areas of the specimens in this study were insufficient to achieve ignition and complete oxidation. However, a comparison to these levels can be made by dividing the amount of material collected in the sampling segment by the amount of oxide formed (mass delta for the coupon). This approach results in a geometric mean ARF×RF of $2\times10^{-4}$ and a maximum ARF×RF of $4\times10^{-4}$. Subsequently, the close alignment between these values indicates appropriate benchmarking of these experiments against those previous studies.

This experiment uses specimens with low specific areas and observed that the aerosol fume appeared to be dominated by sparking. Observations related to the ash:fume ratio indicate that the use of high specific area forms (e.g., chips, machine turnings, saw fines) will result in complete oxidation of the metal. Complete oxidation of the base metal should maximize the amount of aerosol and determine if the ash:fume ratio observations hold true for ignition conditions. This should allow for direct comparison between uranium values for ignition and burning. As such, future work will employ chips and machine turnings of the three alloys used here, as well as any additional alloys identified for study.

The indications that airborne respirable release fractions may be correlated to crystallographic structure will be investigated by using additional alloys of uranium. The U—Mo system with 10 wt % Mo is a γ-phase stabilized alloy with nominally two atoms per unit cell. Other alloys, such as U—Al, will be selected based on availability and number of atoms per unit cell. These alloys will be tested in both the high and low specific area configurations in an attempt to expand the dataset for evaluating the potential correlation between crystallographic structure and aerosol. The calculations for comparison against previous experiments used in the American National Standards Institute (ANSI) and U.S. Department of Energy (DOE) guidance documents will include the same process outlined in this study.

The apparatus designed performs well in all benchmark tests, including producing data directly comparable to the Elder and Tinkle experiments in 1980 and the Carter and Stewart experiments in 1970. Whereas the previous studies used two distinctly different methods for determining respirable aerosol, this experiment allows for a single experimental method that incorporates desired attributes of both experiments. The intent of this experiment is to look for distinct order-of-magnitude differences between the dominant alloys representing distinct metallurgical phases. That objective has been accomplished, demonstrating that the thermal response of U—Ti is significantly higher than the thermal response of other uranium alloys. As such, respirable fractions based on that alloy are not representative of pure uranium or other alloys.

The Elder and Tinkle data used to support the bounding ARF×RF of $1\times10^{-3}$ in DOE guidance appears to be specific to the U—Ti alloy. The Carter and Stewart data supporting the median ARF×RF of $1\times10^{-4}$ in that DOE guidance is appropriate for pure uranium and U—Nb alloys. Both of these values have been benchmarked using the apparatus specifically designed for this experiment indicating that the apparatus can produce data of sufficient quality for use in regulatory applications. Future studies are planned to cement the assertion that there is a demonstrable link between crystallographic structure and respirable aerosol.

This experiment identifies that all uranium alloys are not equal and that there appears to be distinct order-of-magnitude differences between the dominant alloys representing distinct metallurgical phases. The Elder and Tinkle data used to support the bounding ARF×RF of $1\times10^{-3}$ in DOE guidance appears to be specific to the U—Ti alloy. The Carter and Stewart data supporting the median ARF×RF of $1\times10^{-4}$ in that DOE guidance is appropriate for pure uranium and U—Nb alloys.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. An apparatus for the characterization of respirable aerosols, comprising:
   a burn chamber configured to selectively contain a sample that is selectively heated to generate an aerosol;
   a heating assembly disposed within the burn chamber adjacent to the sample; and
   a sampling segment coupled to the burn chamber and configured to collect the aerosol such that it may be analyzed;
   wherein the burn chamber comprises a first spacer disposed therein, the first spacer operable for determining a position of the heating assembly and the sample within the burn chamber; and
   wherein the burn chamber comprises a second spacer disposed therein adjacent to the first spacer, the second spacer selectively containing a material that is selectively combusted or burned and operable for determining the position of the sample within the burn chamber.

2. The apparatus of claim 1, further comprising a sight window disposed in a wall of the burn chamber such that the sample may be viewed during heating.

3. The apparatus of claim 1, wherein the burn chamber comprises a first burn chamber coupled to a second burn chamber.

4. The apparatus of claim 3, wherein the second burn chamber comprises a gas intake conduit operable for introducing a gas into the burn chamber.

5. The apparatus of claim 1, wherein the burn chamber further comprises a grate disposed between the first spacer and the second spacer.

6. The apparatus of claim 1, wherein the sample is selectively disposed on and supported by the second spacer.

7. The apparatus of claim 1, wherein the heating assembly is disposed between the first spacer and the second spacer.

8. The apparatus of claim 1, wherein the heating assembly comprises a spiral heater disposed between a ceramic disc and a quartz disc, the quartz disc operable for preventing the spiral heater from directly contacting a combustible material disposed adjacent to the heating assembly that is selectively burned.

9. The apparatus of claim 1, wherein the sampling segment comprises an aerosol offtake conduit operable for communicating a portion of the aerosol selectively present in the sampling segment to an attached aerosol analyzing system.

10. The apparatus of claim 1, wherein the sampling segment comprises a filter disposed at an end thereof opposite the burn chamber.

11. The apparatus of claim 1, wherein the sample comprises one of a Lanthanide, an Actinide, and a Transition metal.

12. An apparatus for the characterization of respirable aerosols, comprising:
   a burn chamber configured to selectively contain a sample that is selectively heated to generate an aerosol;
   a heating assembly disposed within the burn chamber adjacent to the sample; and
   a sampling segment coupled to the burn chamber and configured to collect the aerosol such that it may be analyzed;
   wherein the heating assembly comprises a heater disposed between a first disc and a second disc, the second disc operable for preventing the heater from directly contacting a material disposed adjacent to the heating assembly that is selectively combusted or burned.

* * * * *